(12) United States Patent
Milgramm et al.

(10) Patent No.: US 7,594,122 B2
(45) Date of Patent: Sep. 22, 2009

(54) METHOD OF DETERMINING WHETHER A TEST SUBJECT IS A SPECIFIC INDIVIDUAL

(75) Inventors: Michael Milgramm, Valley Stream, NY (US); Alex Imas, Niles, IL (US)

(73) Assignee: WaveSynch Technologies, Inc., Forest Hills, NY (US)

( * ) Notice: Subject to any disclaimer, the term of this patent is extended or adjusted under 35 U.S.C. 154(b) by 0 days.

(21) Appl. No.: 12/270,689

(22) Filed: Nov. 13, 2008

(65) Prior Publication Data

US 2009/0156956 A1  Jun. 18, 2009

Related U.S. Application Data

(60) Provisional application No. 60/987,606, filed on Nov. 13, 2007.

(51) Int. Cl.
| | |
|---|---|
| G06F 21/00 | (2006.01) |
| G06F 7/04 | (2006.01) |
| G06F 17/30 | (2006.01) |
| H04L 9/32 | (2006.01) |
| H04L 29/06 | (2006.01) |
| G06F 11/30 | (2006.01) |
| G06F 12/14 | (2006.01) |
| G05B 19/00 | (2006.01) |
| G05B 23/00 | (2006.01) |
| G06F 7/00 | (2006.01) |
| G08B 29/00 | (2006.01) |
| G08C 19/00 | (2006.01) |
| H04B 1/00 | (2006.01) |
| H04B 3/00 | (2006.01) |
| H04Q 1/00 | (2006.01) |
| H04Q 9/00 | (2006.01) |
| G06K 19/00 | (2006.01) |
| A61B 5/04 | (2006.01) |
| A61B 5/05 | (2006.01) |
| A61B 13/00 | (2006.01) |
| G06K 9/00 | (2006.01) |

(52) U.S. Cl. .......................... 713/186; 726/2; 726/26; 713/150; 713/189; 340/5.82; 340/5.52; 600/544; 600/554; 600/558; 902/3; D14/383; D14/480.4; 382/115

(58) Field of Classification Search ....................... None
See application file for complete search history.

(56) References Cited

U.S. PATENT DOCUMENTS 4,582,403 A * 4/1986 Weinblatt .................... 351/210

(Continued)

FOREIGN PATENT DOCUMENTS

WO  WO 2005/004067  1/2005

OTHER PUBLICATIONS

Thorpe, Julie, et al., Pass-thoughts: Authenticating With Our Minds, Proceedings of the New Security Paradigms Workshop, (2005).

(Continued)

*Primary Examiner*—Nasser Moazzami
*Assistant Examiner*—Oscar A Louie
(74) *Attorney, Agent, or Firm*—Gary J. Gershik; Cooper & Dunham LLP

(57) ABSTRACT

This invention provides an EEG-based method of determining whether a test subject is a specific individual.

18 Claims, 6 Drawing Sheets

U.S. PATENT DOCUMENTS

| | | | | |
|---|---|---|---|---|
| 4,652,744 | A | * | 3/1987 | Bowers et al. ......... 250/227.27 |
| 4,941,477 | A | | 7/1990 | Darwell |
| 5,137,027 | A | | 8/1992 | Rosenfeld |
| 5,325,862 | A | * | 7/1994 | Lewis et al. ................ 600/544 |
| 5,762,611 | A | | 6/1998 | Lewis |
| 6,542,081 | B2 | * | 4/2003 | Torch ......................... 340/575 |
| 6,898,299 | B1 | | 5/2005 | Brooks |
| 7,249,263 | B2 | | 7/2007 | Chaudhari et al. |
| 7,461,264 | B2 | | 12/2008 | Chen |
| 2002/0186921 | A1 | | 12/2002 | Schumacher |
| 2002/0188217 | A1 | * | 12/2002 | Farwell ...................... 600/544 |
| 2005/0022034 | A1 | | 1/2005 | Chaudhari et al. |
| 2006/0215883 | A1 | | 9/2006 | Kim et al. |
| 2007/0049844 | A1 | | 3/2007 | Rosenfeld |
| 2008/0005578 | A1 | | 1/2008 | Shafir et al. |
| 2008/0229408 | A1 | | 9/2008 | Dinges et al. |
| 2008/0294907 | A1 | | 11/2008 | Hively |

OTHER PUBLICATIONS

Mohammadi, Galereh, et al., Person Identification Using AR Model for EEG Signals, PWASET, vol. 11, p. 281-285 (Feb. 2006).

Paranjape, R.B., et al., The electroencephalogram as a biometric, Canadian Conference on Electrical and Computer Engineering 2001, vol. 2, p. 1363-1366 (2001).

Palaniappan, Ramaswamy, et al., Novel analysis technique for a brain biometric system, International Journal of Medical Engineering and Informatics 2008, vol. 1, No. 2, pp. 266-273 (2008).

Poulos, M., et al., Person identification based on parametric processing of the EEG, Proceeding of ECECS '99, vol. 1, p. 283-286 (1999).

Poulos, M., et al., Neural network based person identification using EEG features, Proceedings of the ICASSP '99, vol. 2, pp. 1117-1120, (Mar. 15-19, 1999).

Poulos, M., et al., Parametric person identification form the EEG using computional geometry, Proceeding of the ICECS '99, vol. 2, pp. 1005-1008 (Sep. 5-8, 1999).

Palaniappan, Ramaswamy, Electroencephalogram signals from imagined activities: a novel biometric identifier for a small population, Lecture Notes in Computer Science, vol. 4224, p. 604-11 (2006).

Marcel, S., et al., Person authentication using brainwaves (EEG) and maximum a posteriori model adaptation, IEEE Transactions on Pattern Analysis and Machine Intelligence, vol. 29, No. 4, p. 743-8 (Apr. 2007).

Stastny, J., et al., EEG-based biometric person identification, Proceedings 18th International EURASIP Conference Biosignals 2006, p. 76-7 (2006).

Palaniappan, R., Two-Stage biometric authentication method using thought activity brain waves, International Journal of Neural Systems, vol. 18, No. 1, p. 59-66, (May 30, 2008).

Palaniappan, R., et al., EEG Based Biometric Framework for Automatic Identity Verification, Special Issue: Data Fusion for Medical, Industrial, and Environmental Applications, vol. 49, No. 2, p. 243-250 (Oct. 18, 2007.

International Search Report issued Jan. 16, 2009 in connection with PCT International Application No. PCT/US08/12811.

Written Opinion issued Jan. 16, 2009 in connection with PCT International Application No. PCT/US08/12811.

Paranjape, R.B. et al., The electroencephalogram as a biometric, Canadian Conference on Electrical and Computer Engineering 2001, vol. 2, p. 1363-1366 (2001).

Palaniappan, Ramaswamy, et al., Novel analysis technique for a brain biometric system, International Journal of Medical Engineering and Informatics 2008, vol. 1, No. 2, pp. 226-273 (2008) Abstract.

Palaniappan, R., Two-Stage biometric authentication method using thought activity brain waves, International Journal of Neural Systems, vol. 18, No. 1, p. 59-66, (May 30, 2008) Abstract.

* cited by examiner

METHOD OF DETERMINING WHETHER A TEST SUBJECT IS A SPECIFIC INDIVIDUAL

This application claims benefit of U.S. Provisional Application No. 60/987,606, filed Nov. 13, 2007, the contents of which are hereby incorporated by reference.

BACKGROUND OF THE INVENTION

It is a commonly known fact that when one places two conducting electrodes connected to a voltmeter, one on the scalp and the other on an electrically neutral area, such as the mastoids behind the ears, a quantifiable voltage can be observed. This voltage signal and its change with respect to time is the basis of electroencephalography, or EEG. The signal measured on the scalp is actually a summation of individual postsynaptic potentials occurring within the brain. Since both the neural tissue and the skull act as a low pass filter, it is unlikely that the high frequency transients of action potentials would make it up to the scalp, and since postsynaptic potentials generally have lower frequency transients associated with them, it is widely believed that the observed EEG signal originates from them. The EEG recording is characterized by amplitude and frequency and their change over time. The frequency component of the EEG can be utilized to infer the level of an individual's neural activity. The concept of using EEG in authentication of an individual's identity is disclosed herein.

SUMMARY OF THE INVENTION

A method of determining whether a test subject is a specific individual comprising:
 a) recording a first electroencephalograph (EEG) over a first period of time from the specific individual;
 b) exposing the specific individual during the first period of time to a first series of sensory stimuli comprising at least one sensory stimulus familiar to the specific individual and at least four sensory stimuli not familiar to the specific individual, wherein all the sensory stimuli are of the same modality, and quantitating the amplitude of a P300 waveform evoked by the at least one sensory familiar stimulus in the first EEG;
 c) recording a second EEG over a second period of time from the test subject;
 d) exposing the test subject during the second period of time to a second series of sensory stimuli comprising the at least one sensory stimulus familiar to the specific individual and to at least four sensory stimuli not familiar to the specific individual, wherein all the sensory stimuli are of the same modality;
 e) determining from the EEG whether the sensory stimulus familiar to the specific individual evokes a P300 waveform in the test subject and quantitating the amplitude of the P300 waveform so evoked in the second EEG; and
 f) comparing the amplitude of the P300 waveform quantitated in step e) with the amplitude of the P300 waveform quantitated in step b), wherein a P300 waveform quantitated in step e) of greater amplitude than the amplitude of the P300 waveform quantitated in step b) indicates that the test subject is the specific individual, and wherein the failure of the sensory stimulus familiar to the specific individual to evoke a P300 waveform or a P300 waveform quantitated in step e) of the same or lower amplitude than the amplitude of the P300 waveform quantitated in step b) indicates that the test subject is not the specific individual.

DETAILED DESCRIPTION OF THE INVENTION

Figure 1:
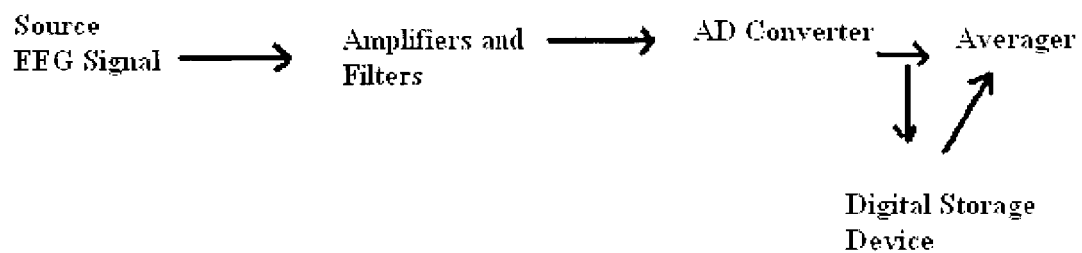
FIG. 1: Path of the raw EEG signal converted to analytical form.

A method of determining whether a test subject is a specific individual comprising:
 a) recording a first electroencephalograph (EEG) over a first period of time from the specific individual;
 b) exposing the specific individual during the first period of time to a first series of sensory stimuli comprising at least one sensory stimulus familiar to the specific individual and at least four sensory stimuli not familiar to the specific individual, wherein all the sensory stimuli are of the same modality, and quantitating the amplitude of a P300 waveform evoked by the at least one sensory familiar stimulus in the first EEG;
 c) recording a second EEG over a second period of time from the test subject;
 d) exposing the test subject during the second period of time to a second series of sensory stimuli comprising the at least one sensory stimulus familiar to the specific individual and to at least four sensory stimuli not familiar to the specific individual, wherein all the sensory stimuli are of the same modality;
 e) determining from the EEG whether the sensory stimulus familiar to the specific individual evokes a P300 waveform in the test subject and quantitating the amplitude of the P300 waveform so evoked in the second EEG; and
 f) comparing the amplitude of the P300 waveform quantitated in step e) with the amplitude of the P300 waveform quantitated in step b), wherein a P300 waveform quantitated in step e) of greater amplitude than the amplitude of the P300 waveform quantitated in step b) indicates that the test subject is the specific individual, and wherein the failure of the sensory stimulus familiar to the specific individual to evoke a P300 waveform or a P300 waveform quantitated in step e) of the same or lower amplitude than the amplitude of the P300 waveform quantitated in step b) indicates that the test subject is not the specific individual.

In an embodiment, the P300 waveform quantitated in step e) is greater than the P300 waveform quantitated in step b) at the 90%, 91%, 92%, 93%, 94% or 95% confidence level. In an embodiment, the P300 waveforms are quantitated using an algorithm.

In an embodiment the P300 waveforms are quantitated using an algorithm.

In an embodiment the EEG is denoised prior to quantitating the amplitude of the P300 waveforms in step b) and in step e).

In an embodiment the test subject is exposed to at least twenty sensory stimuli and wherein the ratio of (a) stimuli not familiar to the specific individual to (b) stimuli familiar to the specific individual to is at least 4:1. In an embodiment the test subject is exposed to no more than thirty sensory stimuli.

In an embodiment the first and second EEGs are each recorded using at least two active electrodes each comprising an Ag—AgCl recording tip.

In an embodiment one electrode records from a Pz site on the test subject's head. In an embodiment the EEG is recorded using at least four electrodes, with three recording from the Pz site on the test subject's head and one recording from a mastoid area of the test subject's head.

In an embodiment the sensory stimuli are visual images. In an embodiment the sensory stimulus familiar to the specific individual is previously provided by the specific individual. In an embodiment the sensory stimuli are auditory.

In an embodiment the method further comprises correcting the first and second EEG for test subject's eye blinks before step f).

In an embodiment the first and second EEGs are corrected for test subject's eye blinks as measured by a fiber-optic eye blink detector.

In an embodiment the test subject is not elicited to provide a continuous account of their thoughts during step d).

In an embodiment the amplitude of the P300 is quantitated by measuring the DX value.

In an embodiment the test subject is informed prior to step c) that if he or she pays attention to the stimuli he or she is more likely to be identified as the specific individual.

In an embodiment each EEG recording is sequentially (a) amplified; (b) filtered through a 30 Hz low pass filter and a 0.3 Hz high pass filter; (c) converted from analog to digital; (d) subjected to a fast fourier transform.

In an embodiment the amplitude of the P300 is determined as the average of at least 20 quantified P300 waveforms.

In an embodiment the test subject is not presented with a target stimulus.

A method of determining whether a test subject has previously been exposed to the information in a predetermined sensory stimulus:

a) recording an electroencephalograph (EEG) over a period of time from the test subject;

b) exposing the test subject during the period of time the predetermined sensory stimulus and at least four sensory stimuli not containing the information in the predetermined sensory stimulus, wherein all the sensory stimuli are of the same modality; and c) determining from the EEG whether the predetermined sensory stimulus evokes a P300 waveform in the test subject, wherein a P300 waveform evoked by the predetermined sensory stimulus in the EEG recorded from the test subject indicates that the test subject has previously been exposed to the information in a predetermined sensory stimulus, and wherein the failure of the predetermined sensory stimulus to evoke a P300 waveform in the EEG recorded from the test subject indicates that the test subject has not previously been exposed to the information in the predetermined sensory stimulus.

In the methods provided the EEGs are recorded using an EEG apparatus.

In an embodiment the amplitude of the P300 waveform is determined from at least 10 sweeps, at least 20 sweeps or at least 30 sweeps.

In an embodiment, the test subject is not presented with a target stimulus.

In regard to the power component ratio, a frequency band power is computed through a Power Spectrum Analysis (PSA) wherein a Fast Fourier Transform (FFT) is applied to the raw EEG signal and a power spectrum is computed ($\mu V^2/Hz$). The spectrum is then condensed and analyzed into frequency bands divided into delta (1-4 Hz), theta (4-8 Hz), alpha (8-12 Hz) and beta (12-20 Hz) components. Power component ratios are then determined by dividing the power of the particular frequency band by the sum of the powers of all of the recited frequency bands. Thus an alpha power component ratio would be:

Alpha power/(delta power+theta power+alpha power+beta power).

In embodiments the alpha waveband power component ratio is 0.5, 0.55, 0.6, 0.65, 0.7, 0.75, 0.8, 0.85, 0.9, 0.95, or 1.0, or any range thereof, when the theta waveband power component ratio is less than 0.5.

In embodiments the theta waveband power component ratio is 0.5, 0.55, 0.6, 0.65, 0.7, 0.75, 0.8, 0.85, 0.9, 0.95, or 1.0, or any range thereof, when the alpha waveband power component ratio is less than 0.5.

Where a range is give it is understood that the range includes all integers and 0.1 units within that range, and any sub-range thereof. For example, a range of 30 minutes to 24 hours includes the times 31 minutes, 32 minutes etc., as well as the ranges 45 minutes to 55 minutes, 44 minutes to 59 minutes, etc.

It is understood that the method described herein can be used to authenticate a subject's identity to permit access control, i.e. access to computers, buildings, databanks, etc.

Every embodiment described herein may be performed employing a computer and associated relevant apparatus as described herein.

All combinations of the various elements described herein are within the scope of the invention.

EXPERIMENTAL DETAILS

EEG recording and the apparatus that may be used therefor are described in Allison et al., U.S. Patent Application Publication No. 2005/0017870; Preston, U.S. Pat. No. 5,267,570; Gevins, U.S. Pat. No. 5,724,987; Gevins, U.S. Pat. No. 5,447,166; Gevins, U.S. Pat. No. 5,295,491; Maynard, U.S. Pat. No. 5,816,247; Burton, U.S. Patent Application Publication No. 2004/0044293; Levendowski et al., U.S. Pat. No. 6,625,485; Levendowski et al., U.S. Pat. No. 6,496,724; Johnson, U.S. Pat. No. 6,754,524; Moore-Ede, U.S. Pat. No. 6,511,424; Moore-Ede, U.S. Pat. No. 6,070,098; and Pavelka, WO 2006/000166, each of which is hereby incorporated by reference.

Traditionally, an EEG was recorded using hollow disk electrodes made from tin, silver or gold. The electrodes were attached to the subject's scalp using conduction paste in order to minimize noise and impedance of the signal. The subject's scalp had to be prepared by cleansing the areas involved in the experiment usually through abrasion. Recently, a new type of electrode has been developed that functions through an active setup. The electrode is able to tolerate high levels of impedance and consequently prior skin preparation is no longer necessary. The new electrode, available as for example the BioSemi Pin-Type active electrode, contains an Ag—AgCl tip which eliminates most noise and significantly lowers signal impedance. The electrode is fitted into specially designed holders on the BioSemi headcap which are filled with electrode gel through a syringe. The elastic headcap is then fitted atop the subjects head and the EEG data collection can begin. The technology disclosed herein can employ the active electrode setup so as to minimize time and participant discomfort. After the electrode holders are filled with gel and the appropriate electrodes are attached, the electroencephalogram of many individuals can be obtained without any further setup.

The individual in charge of running the biometric technology replaces the electrode gel as needed.

In order to record EEG, a minimum of two electrodes is necessary. One electrode must be placed at the reference point and another at the site of interest. The reference point should be electrically neutral so as to act as a baseline (different from the pre-signal baseline used to measure ERPs) which coupled with the signal from the electrode on the scalp will be used to calculate the EEG voltage potential readings. Typically the mastoids or the ears are used as the reference point: the mastoids being well insulated by a particularly thick layer of bone to impede the signal and the ears being far enough from the signal source to pick up anything substantial.

The EEG signal can be distorted by external noise signals which have a variety of sources. The source of noise that would most significantly affect the technology is blinking. When an individual blinks it causes a significant jump in the voltage potential that may be interpreted as an event related potential. Several techniques have been developed to eliminate the influence of this artifact. Many practitioners apply two additional electrodes for electrooculography (EOG) recording diagonally above and below the eye to pick up vertical and horizontal eye movements. When the voltage potential from those two electrodes exceeds a certain threshold, over 80 µV in most protocols, that particular trial is disregarded as containing an artifact so that only error-free trials are kept. This is accomplished through a program, introduced by Gratton, Coles and Donchin in 1983 and further developed by Ziegler and Gattaz in 1992, which determines the magnitude of correlation between eye electrodes' vertical and horizontal leads and the EEG signal. For the purposes of the technology described here, the number of electrodes necessary for EEG recording can be minimized by an eye sensor that detects blinks, such as the Fiber-Optic Eye-Blink Switch (PSSW-EB), that is used to detect blinks and then signal for the EEG recording program to eliminate those trials. This will eliminate the need for EOG recording.

FIG. 1 describes the path of the raw EEG signal as it is converted into a form that is usable for analytical purposes. The signal is first passed through amplifying and filtering systems which increase the strength of the signal, accentuate the desired portions and filter out any unwanted frequencies. The gain should be set high enough so that the amplitude is sufficiently sensitive to pick up small deflections, but low enough so that saturation or clipping does not occur. The filtering system should couple a low pass and high pass filter in order to control for noise or artifacts. A typical protocol for recording P300 ERPs sets the low pass filter at 30 Hz and the high pass filter at 0.3 Hz (Rosenfeld et al 2003). The modified signal is then sent to an Analog to Digital Converter (A/D Converter) which samples the analog signal, typically at 100 Hz, and converts the data into a digital stream. The EEG recording is now usable for software analysis. Applying a Fast Fourier Transform (FFT) at this point decomposes the complex signal into its underlying sine wave constituents, and a frequency band diagram can be composed that illustrates the prominence of different frequencies in the subject's EEG recording.

Event Related Potential:

For the purposes of the technology disclosed here a particular component is analyzed of the EEG called the Event Related Potential (ERP). Essentially, the ERP is the body's psychophysiological response to a given stimulus. Since individual neurons have relatively little electrical activity associated with them, certainly not enough to be detected on the scalp, ERPs are recorded when neurons act synchronously and the electric fields generated by each particular neuron are oriented in such a way that the effects on the scalp cumulate. Only neurons organized in a layered open field manner (neurons with dendrites and axons oriented in the same fashion) are picked up as an ERP. Given that property, an infinite amount of generators in different parts of the brain can be producing the ERP; just because an ERP is detected in a certain place on the scalp does not mean that it is being generated from a single area within the brain—you can infer location of surface activity but not internal activity. Stimuli that cause ERPs can either be external, such as the memory coupled stimulus that invokes the P300, or internal, such as the rhythmic pacemaker-like oscillations projected by the nucleus reticularis to thalamic nuclei and the cortex.

Figure 2:
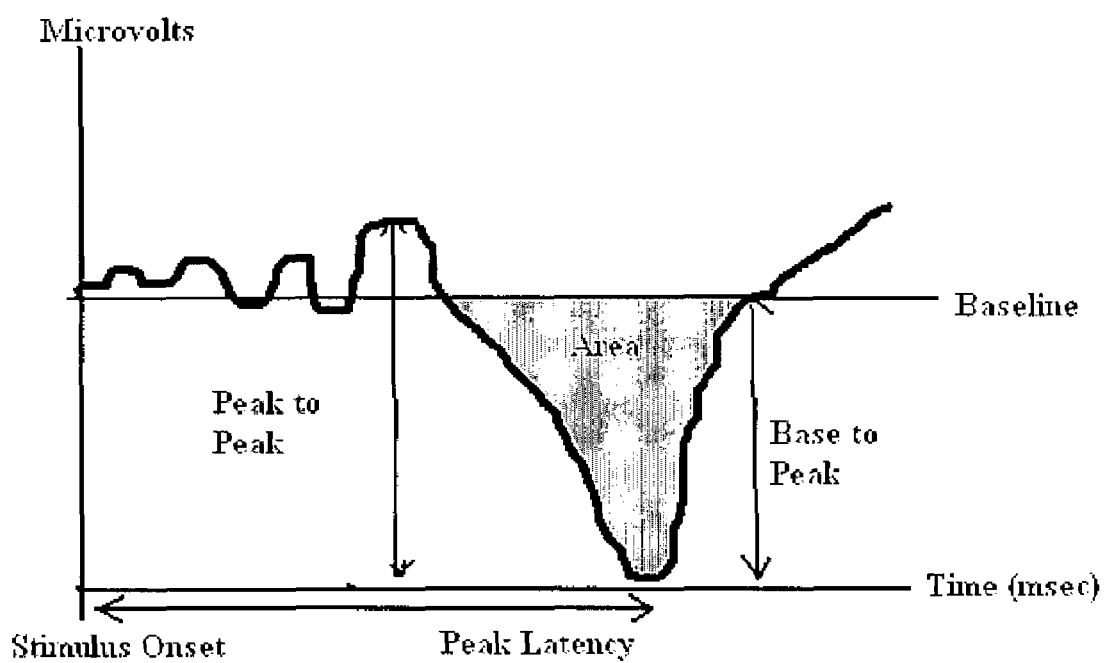
FIG. 2: P300 waveform

ERPs are generally small, about 50 µV, in comparison to the overall EEG recording. Hence, in order to perform an analysis on it the discrimination of the signal must be increased from the background noise of the general EEG. In order to accomplish this, the EEG recording is sent to the Averager. In order to average out the EEG noise, the ERP signal must be constant over trials, the noise must be random across trials and the ERP signal must be independent of background noise. Therefore, because the ERP signal is time locked, the EEG background noise can be averaged out leaving only the desired ERP signal. The number of samples used in the average is related to the signal to noise ratio, so a minimum of 20 samples must be used to produce a viable ERP. The result is a voltage vs. time function containing a number of positive and negative peaks. ERPs are described in terms of their characteristic scalp distribution, polarity and latency; a typical ERP readout (in this case the P300) is pictured in FIG. 2.

The P300 Waveform:

The P300 is a specific ERP component that is characterized as a psychophysiological response to rare and significant stimuli. For example, if a subject is presented with a set of photographs in which most depict the faces of neutral people (to the individual) and some depict the faces of recognizable people, such as the subject's mother, then the recognizable pictures will evoke a P300 in the individual. A P300 is also evoked when the rare stimulus is explicitly task relevant, such as when the individual is asked to press a button only when that particular stimulus is displayed. The amplitude of the P300 is sensitive to the relevant stimulus' probability, so it is important to make them sufficiently rare (typically a 1:4 ratio of relevant to irrelevant stimuli is used). The waveform can be elicited by stimulus classes in any modality as long as the subject can identify them unambiguously. Various classes of auditory and visual stimuli have been shown to evoke the P300. Amplitude is also related to the processing resources that are demanded by a particular task. Donchin, Kramer and Wickens showed in a 1986 study that the P300 amplitude increases in response to a primary task and decreases in response to a secondary task, meaning the more an individual is paying attention the larger the P300 amplitude evoked. As a result, its amplitude is greater in high reward situations, such as when a person is trying to be identified properly, than in low reward situations, because it is in the person's best interest to pay more attention when they know there is a benefit in it (Brookhaven Neuropsychoimaging Group, 2003). Since self-relevant information demands high order cognitive processing, and therefore a high degree of brain resources, using autobiographical information as the stimulus for a subject that wants to recognize will maximize the amplitude of the evoked P300. Intrinsic psychological relevance is also a factor, so the more "emotional value" a subject assigns to a piece of autobiographical information the larger their P300's amplitude (Gray, Ambady et al, 2003).

There are two main theories that attempt to explain the P300 waveform. The Context Updating theory (Dochin, 1981; Dochin, Karis et al, 1986; Dochin, Coles, 1988a; 1988b) states that the P300 is evoked through the brain's active information processing of a given relevant stimulus. In response to the stimulus, the models or contexts of the working memory are updated as the information represented in the stimulus is integrated into the individual's internal representation of the environment. The manifestation of the P300 may indicate the end of that processing. Many studies have shown that indeed this theory holds true, although it's exclusivity in explaining the P300 has not been confirmed. Studies in the field of autobiographical memory have shown that a P300 can be evoked even when the given stimulus is task-irrelevant. When a stimulus pertaining to a subject's life experiences, such as a picture of his mother or wife, is displayed amongst wholly irrelevant stimuli, a large P300 is evoked. The explanation for this states that the inherent relevance of this stimulus, namely that the subject is automatically forced to recall the life events associated with it and integrate the presentation of the stimulus into his brain's internal model, invokes the context updating process that is responsible for the manifestation of the P300.

Another theory states that the P300 is the result of a momentary deactivation of the cortex (Desmedt, 1980). Given that most P300 based studies inform the subject that a task-relevant stimulus will be presented to them during the trials, this theory proposes that the individual's cortex is activated in anticipation of that task-relevant stimulus appearing, and becomes deactivated when that stimulus arrives. This deactivation of the cortex produces the transient positivity that characterizes the P300 waveform. After the stimulus passes, the individual again begins to anticipate the next task-relevant stimulus and the cortical negativity resumes. It must be noted that individuals will exhibit a lower P300 response if they are either schizophrenic, suffer from PTSD, or late stage Alzheimer's.

The P300 is characterized by a positive peak with a modal latency of 300 msec and is best measured at the Pz site on the scalp. The Peak to Peak method is typically used to measure the amplitude of the peak. The 300 to 900 msec window of the ERP is searched for the largest positive segment average of 100 msec, with the midpoint of that segment being the latency. A 100 msec average segment corresponding to the maximal negativity is then found by looking between the calculated positive segment and the 1000 msec mark. The difference between the two segments is the DX value. This value has been found to be more sensitive in P300 based studies (e.g., Soskins, Rosenfeld, & Niendam, 2001) than the MX value which is calculated by taking the difference between the pre-stimulus EEG measurement and the maximally positive segment.

Current Applications of the P300

Though many ERP's have been discovered since the advent of EEG technology, the P300 remains the most studied amongst them due to its reliability and consistency. A number of methods have been designed for a variety of applications that are structured around the P300 and its properties as a signal of memory recall. Two of the major protocols currently being tested include the Farwell Truth Detector and the Rosenfeld Complex Trial Protocol (CTP) for the detection of concealed information. Both of the protocols are designed as a replacement for the polygraph in the field of lie detection. The suspected individual, who, if guilty, is presumed to know the details surrounding the offense that he had committed, is presented with a series of irrelevant stimuli which are interspersed with relevant stimuli that contain information about the particular crime that is theoretically only known by the investigator and the offender. The relevant stimulus is called the probe and the irrelevant stimuli are called the irrelevants. A third class of stimuli is included which are also irrelevant to the individual. They are associated with a task that the individual is assigned to perform beforehand whenever he encounters them. These stimuli are called the targets and they are included in order to make sure that the individual is paying attention. If the subject continuously fails to perform the task assigned he can be charged with being non-cooperative. The two protocols have different twists on this scheme, but essentially a typical session has the subject sitting down in front of a monitor with 7 passive electrodes placed on his head: 3 on the scalp, Pz, Cz and Fz, two on the linked mastoids, two above and below the eye, and one ground in the middle of the forehead. The monitor then displays the stimuli in succession between 150-300 times as the subject uses a keypad to signal that they saw each stimulus and performed the assigned target stimuli tasks. The theory behind these protocols is that the relevant stimuli would only elicit a P300 in the guilty subjects, while the innocent subjects would have essentially the same electroencephalogram for the probes as irrelevants.

In order to determine guilt, the experimenter must determine if the average size of the probe P300 is larger than the average size of the irrelevant P300 to a statistically significant degree, using a confidence interval of either 90 or 95%. In order to do this one must have a distribution of average P300 waves. This would require a population study which is outside the scope of most research. The bootstrap method addresses this issue by creating an average distribution of P300 waves for each individual studied by going through the single sweep probe set and drawing with replacement a set of waveforms that equals the total number of probe sweeps. The same method is then applied to the irrelevant set, creating a set of waveforms that numbering the total irrelevant sweeps. Each set is then averaged and a DX value of the P300 is calculated. The DX value from the irrelevant mean is then subtracted from the DX value of the probe mean and that difference is placed in a distribution which will contain, after 100 iterations of the above method, 100 values. In order to say with 90 percent confidence that a probe response is indeed larger than the irrelevant response, the distribution calculated through the bootstrap method must not contain 0 more than 1.29 standard deviations below the mean. If 0 is not present within the given confidence interval, the null hypothesis that the average probe is not different than the average irrelevant can be rejected with respect to the given alpha value, 0.1. This method has the advantage of using all of the data available while simultaneously being more sensitive to single sweep data than a t-test (Rosenfeld et al., 1991).

A third protocol utilizing the P300, also developed by Farwell, is designed to detect knowledge not necessarily regarding a specific incident, but rather a more generalized class of information that would be possessed only by individuals with particular occupational knowledge or professional expertise. In addition, the targets are a subset of the relevant stimuli (Farwell 1992). The potential application of this protocol would be to identify individuals who possess a specific type of background information (e.g., military or intelligence expertise). Since the individual does not know what stimuli they are going to be presented with in advance and there are no previous records of an individual's response to a particular stimulus, the protocol is similar to the one used in detecting concealed information.

P300 as a Novel Biometric Security Indicator

In utilizing the P300 in a biometric security technology, a novel protocol has been developed as disclosed herein. The individual using this technology wants to be identified, in the same way as a person using a fingerprint scanner wants to have a positive identity match. This differs significantly from the ideas behind the protocols described above which are meant to detect information that the subject does not necessarily want the investigator to know. In this setting, subject is involved in a scenario where detection is a high reward scenario instead of a low reward one. In addition, it is in the best interest of the subject to pay attention to the stimuli since if he does not, his chances of a positive ID match are lowered. If he is informed of this fact beforehand, the protocol can effectively involve only relevant and irrelevant stimuli without the need for targets or assigned confirmation tasks since attention is more or less guaranteed. In short, targets (i.e. stimuli which are irrelevant to the individual and are associated with a task that the subject is assigned to perform) are not required, and are excluded from this protocol.

Since this technology can function like an identity confirmation device, much like a fingerprint or iris scanner, the subject is himself should be responsible for submitting information that will later be used to identify him. In the technology, that information will consist of a series of self-selected autobiographical images that the subject will submit to the biometric database. Examples may include pictures of the individual's dog, house, wife, license plate etc; essentially anything that he finds personally relevant, and the more relevant the better. When using this device, a relevant image provided by the individual will be displayed amongst a large number of irrelevant images of the same subclass. When the relevant image comes up it can evoke the P300 brainwave and identify the individual. If no significant P300 response is evoked, it can be concluded that there is no identity match, and the individual can either be denied entry or be subjected to a subsequent session. The bootstrapping method will be utilized to determine if there is a significant difference between the relevant and irrelevant stimuli. Due to the desire of the individual to be identified and the fact that the relevant stimuli set consist of self-selected autobiographical stimuli, the brain resources devoted to the primary task will be significantly larger than in the previously described protocols. Therefore, the evoked P300 response will be significantly larger in magnitude.

In addition, the self-selection of the relevant stimulus list satisfies both theories pertaining to the P300, while the protocols above rely solely on the validity of the Context Updating Theory. Agreement with the Context Updating Theory is self-explanatory since the stimulus list consists of autobiographical information that will trigger memory recall and model revision. The self-selection element of the protocol agrees with the cortex activation/deactivation theory in that since the individual knows in advance what stimuli he has to look for in order to be identified, they will act as oddballs amongst the irrelevant stimuli and trigger cortical deactivation once they appear and remove the anticipation. This fact has the potential to increase the evoked P300 response even further. Consequently the new protocol would involve 4 electrodes, 3 on the Pz site (for reasons that will be explained below) and 1 reference on the mastoids. In addition, the number of trials required to verify the individual's identity will range between 20 to 30 since in the case of an identity match, the relevant stimulus would evoke a very large P300 in comparison to the irrelevant stimuli and it would therefore take less iterations to confirm a significant difference.

The relevancy of a given stimulus may change over time: an individual who divorces from his wife may slowly begin to forget her, and therefore her image would evoke a less prominent P300 peak. This process can be referred to as time-dependent relevance decay. The self-selection of the stimulus would still keep its oddball relevancy strong, but nonetheless the P300 response may still possibly lessen over time. Second, a person trying to pose as a particular individual may also be familiar with a particular stimulus that the individual had chosen, and its presentation would consequently also evoke a P300 response in the impostor. For example, if a robber trying to get into a building is shown an image of a particular tenant's wife, and the robber had seen her around the building before, a P300 response would be evoked. In order to address both considerations, the biometric technology must be calibrated prior to use by every individual whose identity information is in the biometric database. The calibration process would consist of a test run during which the individual is presented with each stimulus on his stimulus list interspersed amongst irrelevant stimuli, accordingly. The averaged P300 response to each self-selected stimulus would be recorded and stored in the system along with the individual's identity information. When the biometric technology is then later used on that person, the ERP results will be tested for significance using the bootstrap method first against the same-session irrelevant stimuli recordings, and then against the stored P300 response gathered for that particular stimulus during calibration. A person who fails the first test of significance will be denied access since that shows that he is not familiar with the relevant stimulus to any significant degree. A person who passes the first test of significance but fails the second will be asked to repeat the session with a different stimulus, since at that point identity can neither be confirmed nor denied—a lack of attention or the stimulus' time-dependent relevance decay may be responsible for the decrease in P300 response. The same statistical methods will then be applied to the results, and if the same scenario keeps occurring for every stimulus on the individual's claimed stimulus list, he will be denied entry and asked to submit a new stimulus list to be recalibrated at a later time. It is therefore important that the individual updates his stimulus list periodically so as to avoid that situation.

This component of the protocol addresses both of the above considerations in the following ways. It takes the time-dependent relevance decay of a particular stimulus into account by asking the individuals to continuously update their stimulus list. In addition, a person less familiar with the stimulus than the individual who selected it would show a significantly smaller P300 response. Therefore, an impersonator, even if he is familiar with a certain stimulus, would be asked to repeat the session with a different stimulus before being granted access, and will end up being denied access altogether when he fails to show a strong enough P300 response to any of the stimuli on the list or encounters a stimulus that he is wholly unfamiliar with. Using the above example again, the tenant's wife will not nearly have as much personal relevance to the robber as she does to the tenant, and therefore he will be denied entry.

The technology can also be used as a biometric security system for limiting access to computers. The screensaver installed on the computer to be protected would display a set of images at discreet intervals, consisting of irrelevant images interspersed with relevant images that the individual submits into the database. The protocol for granting the person access to the computer would closely resemble the one used for the more general identity confirmation technology described above. Once the individual sits down in front of the computer and puts on the EEG helmet, this time without the LCD screen, the system would read his ERP readings to each of the images displayed in the screensaver. If he or she generates a P300 for the relevant images that is significantly higher than the one generated for the irrelevant images, access is granted to the system. The same statistical methods are used to gauge significance as described above.

Figure 3:
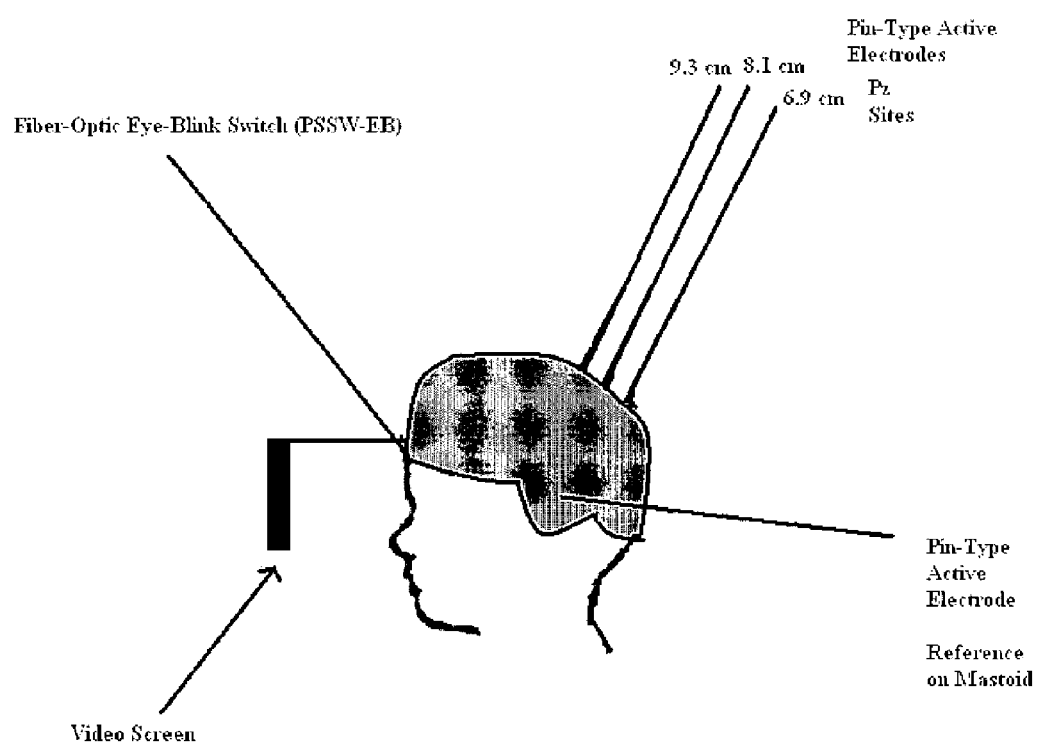
FIG. 3: EEG recording apparatus with active electrodes and fiber-optic blink switch and device for presenting image.
Figure 4:
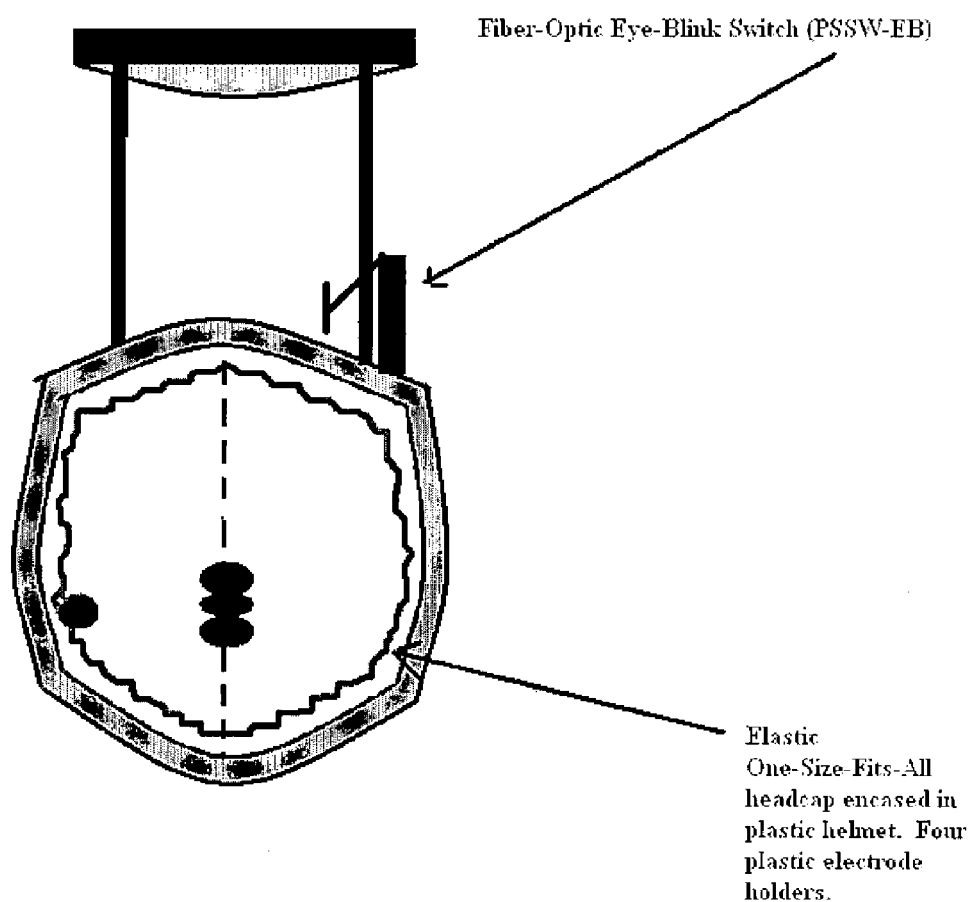
FIG. 4: Top view of device in FIG. 3.

The Device:

In order to insure the commercial viability of the biometric technology, the design associated with it must allow the technology to be used quickly, efficiently and by a significant sub set of the population. The elements that receive and modify the raw EEG signal can be effectively implemented in their current state. The technology that collects the actual EEG signal on the other hand can be modified in order to meet the requirements mentioned above. A design for this device is depicted in FIGS. 3 and 4.

Figure 5:
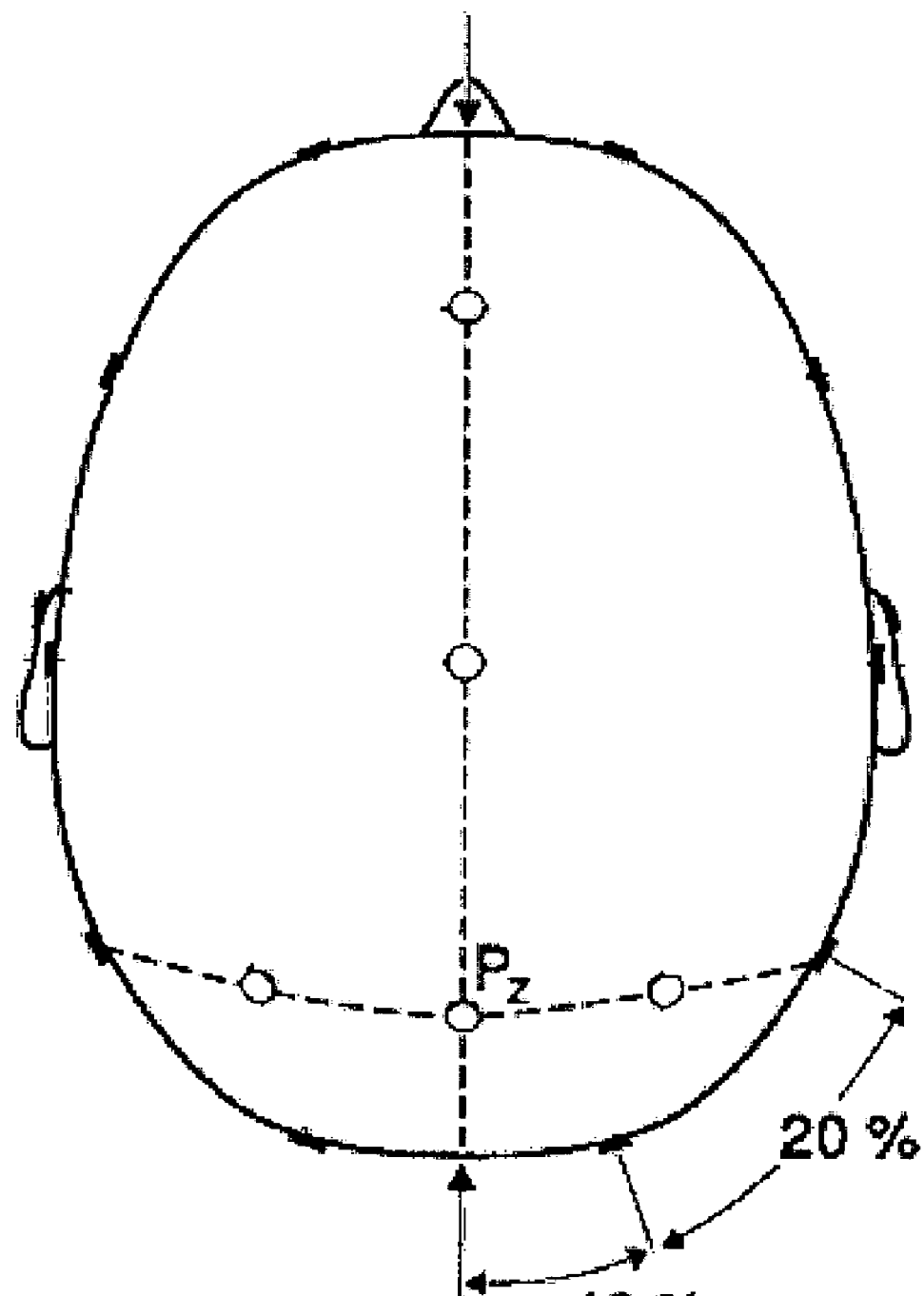
FIG. 5: Position of Pz recording site on skull.

The outside of the device consists of a plastic helmet measuring between 62-66 cm in circumference, able to fit most individuals since head circumferences typically range between 46-62 cm. The helmet has 4 holes for the electrode holders, allowing them to be filled periodically with electrical gel by the person who maintains it. As mentioned above, the use of active electrodes eliminates the need for scalp cleansing and therefore cuts the prep time for EEG recording to significantly nothing. The 3 electrode holders at the top of the helmet are meant for the recording Pz EEG signals. FIG. 5 shows the location of the Pz site on an individual's scalp.

Since typical head circumferences range between 46-62 cm, the 20% mark of the Pz site lies 6.9-9.3 cm from the vertical midline. Therefore, in order to insure that the EEC signal is being recorded from the Pz site of every individual, 3 electrodes are placed 6.9 cm, 8.1 cm and 9.3 cm from the vertical midline of the helmet, respectively. The signals from each electrode are then averaged to produce a single EEG recording. This allows the technology to be used on most individuals without having to worry about different sizes for the device.

The inside of the helmet contains an elastic headcap, similar to the one designed by BioSemi, to which the electrode holders are actually attached. It will comfortably fit on the heads of most individuals and allow for maximal proximity of the electrodes to the scalp. A Fiber Optic Eye Blink Switch attached to the front of the helmet will detect blinks and signal the recording software to eliminate the implicated trials. This eliminates the need for EOG recording and makes the process of gathering data more comfortable for the individual because there are no electrodes or device protrusions touching his face. A video screen is attached to the front of the helmet and displays the appropriate visual stimuli. It works in conjunction with the EEG recording software and presents stimuli according to the conditions set by the individual running the technology. This makes the technology significantly more versatile in that it can be used in any space containing a personal computer and signal processing devices, such as a building lobby or an office.

The biometric database associated with the technology will consist of three parts. The first part will be the series of self-selected autobiographical images that the individual using this technology submits to the administrator. Each image will be tagged with a specific category (an image of the individuals elderly mother will be categorized as <woman, 50+>) and placed inside the person's personal directory along with the date when it was submitted. The second part of the database will be created during the calibration process after the submitted images have been processed accordingly. The P300 readout recorded during calibration, against which the second phase of the bootstrap process will be testing against, will be placed within the individual's personal directory as well, and associated with the stimulus image it was recorded in response to. The P300 readout will also be tagged with the date and time at which it was taken to insure that the individual is regularly recalibrating his biometric directory. The third component of the database consists of a large set of images which will be used as the irrelevant stimuli during the identification process. Each image will be assigned to a category, so when the relevant stimulus is in the category <woman, 50+>, as in the previous example, the irrelevant stimuli will be chosen from the image set that also fits within that category.

Figure 6:
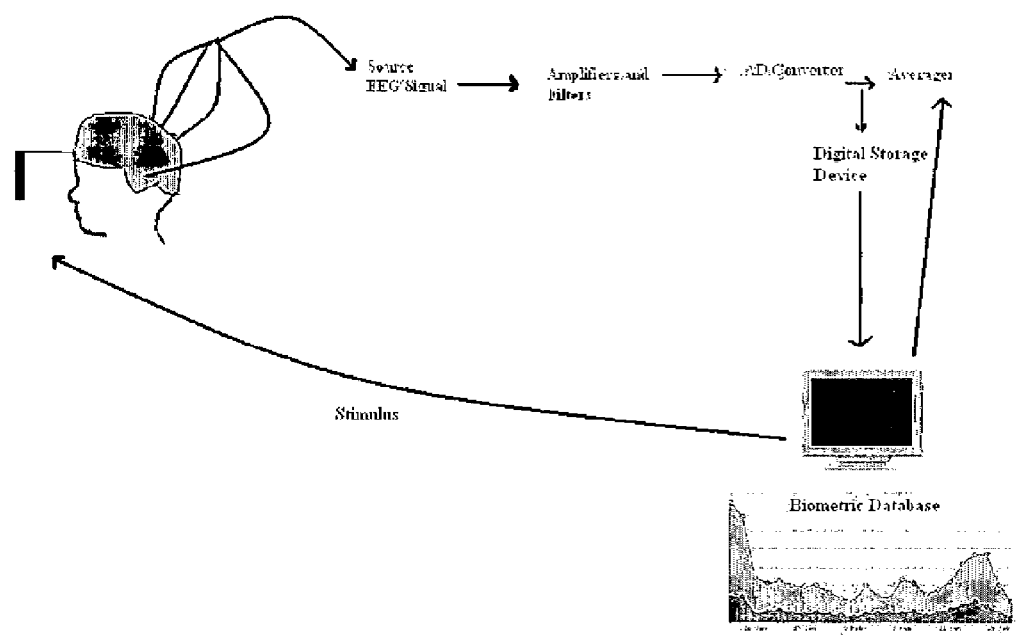
FIG. 6: EEG recording apparatus showing stimulus providing apparatus and biometric database.

FIG. 6 is a representation of the technology.

A subject, who has previously provided an image with which the subject is familiar, is attached to a BioSemi electrode-type EEG recording apparatus. The EEG is recorded and the subject is exposed to a first series of images comprising the image familiar to the specific individual and at least four images not familiar, or not known to be familiar, to the specific individual. The subject's P300 waveform evoked by the familiar image is determined from the EEG and quantitated. A period of time is permitted to pass and the subject, from whom an EEG is being recorded, is subjected to a second series of images comprising the familiar image and at least four images not familiar to the subject. It is determined from the EEG whether the image familiar to the subject evokes a P300 waveform in the subject and the P300 waveform is quantified. The second P300 waveform amplitude is found to be of greater amplitude than the amplitude that the first P300 waveform quantitated, thus indicating that the test subject is the specific individual to be identified.

The amplitude/DX value of the P300 waveforms may be determined from a single sweep or from a number of sweeps, e.g. at least 10, at least 20 or at least 30. The signal can be sequentially (a) amplified; (b) filtered through a 30 Hz low pass filter and a 0.3 Hz high pass filter; (c) converted from analog to digital; (d) subjected to a fast fourier transform and then analyzed to determine the principal components, e.g. by frequency.

A subject who has previously provided an image with which the subject is familiar is attached to a BioSemi electrode-type EEG recording apparatus. The EEC is recorded and the subject is exposed to a first series of images comprising the image familiar to the specific individual and at least four images not familiar, or not known to be familiar, to the specific individual. The subject's P300 waveform evoked by the familiar image is determined form the EEG and quantitated. A period of time is permitted to pass and a test subject, from which an EEG is being recorded, is subjected to a second series of images comprising the familiar image and to at least four images not familiar to the subject. It is determined from the EEG whether the image familiar to the subject evokes a P300 waveform in the test subject and the amplitude of the second P300 waveform is found to be less that the initial P300 waveform, thus indicating that the test subject is not the subject to be identified.

What is claimed is:

1. A method of determining whether a test subject is a specific individual comprising:
   a) recording a first electroencephalograph (EEG) over a first period of time from the specific individual;
   b) exposing the specific individual during the first period of time to a first series of sensory stimuli comprising at least one sensory stimulus familiar to the specific individual and at least four sensory stimuli not familiar to the specific individual, wherein all the sensory stimuli are of the same modality, wherein the test subject is exposed to at least twenty sensory stimuli and wherein the ratio of (a) stimuli not familiar to the specific individual to (b) stimuli familiar to the specific individual to is at least 4:1, and quantitating the amplitude of a P300 waveform evoked by the at least one sensory familiar stimulus in the first EEG;

c) recording a second EEG over a second period of time from the test subject;

d) exposing the test subject during the second period of time to a second series of sensory stimuli comprising the at least one sensory stimulus familiar to the specific individual and to at least four sensory stimuli not familiar to the specific individual, wherein all the sensory stimuli are of the same modality;

e) determining from the second EEG whether the sensory stimulus familiar to the specific individual evokes a P300 waveform in the test subject and quantitating the amplitude of the P300 waveform evoked in the second EEG; and f) comparing the amplitude of the P300 waveform quantitated in step e) with the amplitude of the P300 waveform quantitated in step b), wherein sensory stimuli are irrelevant, relevant and target stimuli, and wherein the sensory stimuli familiar to the specific individual is previously provided by the specific individual, and wherein the test subject is only presented with irrelevant and relevant stimuli, and wherein a P300 waveform quantitated in step e) of greater amplitude than the amplitude of the P300 waveform quantitated in step b) indicates that the test subject is the specific individual, and wherein the failure of the sensory stimulus familiar to the specific individual to evoke a P300 waveform or a P300 waveform quantitated in step e) of the same or lower amplitude than the amplitude of the P300 waveform quantitated in step b) indicates that the test subject is not the specific individual.

2. The method of claim 1, wherein the P300 waveforms are quantitated using an algorithm.

3. The method of claim 1, wherein the EEG is subject to a fast fourier transform prior to quantitating the amplitude of the P300 waveforms in step b) and in step e).

4. The method of claim 1, wherein the test subject is exposed to no more than thirty sensory stimuli.

5. The method of claim 1, wherein the first and second EEGs are each recorded using at least two electrodes each comprising an Ag—AgCl recording tip which electrodes are active electrodes.

6. The method of claim 5, wherein one electrode records from a Pz site on the test subject's head.

7. The method of claim 1, wherein the EEG is recorded using at least four electrodes, with three recording from the Pz site on the test subject's head and one recording from a mastoid area of the test subject's head.

8. The method of claim 1, wherein the sensory stimuli are visual images.

9. The method of claim 8, wherein the sensory stimulus familiar to the specific individual is previously provided by the specific individual.

10. The method of claim 1, wherein the sensory stimuli are auditory.

11. The method of claim 1, further comprising correcting the first and second EEG for test subject's eye blinks before step f).

12. The method of claim 11, wherein the first and second EEGs are corrected for test subject's eye blinks as measured by a fiber-optic eye blink detector.

13. The method of claim 1, wherein the test subject is not elicited to provide a continuous account of their thoughts during step d).

14. The method of claim 1, wherein the amplitude of the P300 is quantitated by measuring a DX value of the P300.

15. The method of claim 1, wherein the test subject is informed prior to step c) that if he or she pays attention to the stimuli he or she is more likely to be identified as the specific individual.

16. The method of claim 1, wherein each EEG recording is sequentially (a) amplified; (b) filtered through a 30 Hz low pass filter and a 0.3 Hz high pass filter; (c) converted from analog to digital; (d) subjected to a fast Fourier transform.

17. The method of claim 1, wherein the amplitude of the P300 is determined as the average of at least 20 quantified P300 waveforms.

18. The method of claim 1, wherein the EEGs are recorded using an EEG apparatus.

* * * * *